(12) United States Patent
van Es et al.

(10) Patent No.: US 7,932,353 B2
(45) Date of Patent: Apr. 26, 2011

(54) NON-GLYCOSYLATED RECOMBINANT COLLAGEN-LIKE POLYPEPTIDES

(75) Inventors: Andries Johannes Jozef van Es, Udenhout (NL); Jan Bastiaan Bouwstra, Bilthoven (NL); Peter Franciscus Theresius Maria van Asten, Hilvarenbeek (NL)

(73) Assignee: Fujifilm Manufacturing Europe B.V., Tilburg (NL)

( * ) Notice: Subject to any disclaimer, the term of this patent is extended or adjusted under 35 U.S.C. 154(b) by 465 days.

(21) Appl. No.: 11/817,006

(22) PCT Filed: Feb. 22, 2006

(86) PCT No.: PCT/NL2006/050030
§ 371 (c)(1),
(2), (4) Date: Jan. 16, 2008

(87) PCT Pub. No.: WO2006/091099
PCT Pub. Date: Aug. 31, 2006

(65) Prior Publication Data
US 2008/0107666 A1    May 8, 2008

(30) Foreign Application Priority Data

Feb. 23, 2005  (EP) .................................... 05075439

(51) Int. Cl.
*A61K 38/17*  (2006.01)
*C12N 15/00*  (2006.01)

(52) U.S. Cl. ........................................ 530/356; 435/440

(58) Field of Classification Search ................... 530/356
See application file for complete search history.

(56) References Cited

U.S. PATENT DOCUMENTS

2003/0064436 A1    4/2003   Vaughan et al.

FOREIGN PATENT DOCUMENTS

| EP | 0 014 176 | | 8/1980 |
| EP | 0 926 543 | A1 | 6/1999 |
| EP | 0 273 308 | A1 | 1/2003 |
| EP | 1 398 324 | A1 | 3/2004 |
| WO | WO 01/34646 | A2 | 5/2001 |
| WO | WO 2004/075871 | A1 | 9/2004 |

OTHER PUBLICATIONS

Vitagliano et al. "Structural Bases of Collagen Stabilization Induced by Proline Hydroxylation", Biopolymers, 2001, vol. 58, pp. 459-464.*
Bretthauer and Castellino, "Glycosylation of Pichia pastoris-derived proteins", Biotechnol. Appl. Biochem (1999) 30, 193-200.
Van den Steen et al, "Concepts and Principles of O-Linked Glycosylation," Critical Reviews in Biochemistry and Molecular Biology, 33(3): 151-208 (1988).
Felix Franks, "Long-Term Stabilization of Biologicals", Biotechnology vol. 12 (Mar. 12, 1994).

* cited by examiner

*Primary Examiner* — Suzanne M. Noakes
(74) *Attorney, Agent, or Firm* — Gilberto W. Villacorta; Sunit Talapatra; Foley & Lardner LLP

(57) ABSTRACT

The invention relates to recombinant collagen like polypeptides that are not glycosylated thereby reducing the immunogenicity of recombinant collagen-like polypeptides while at the same time preventing or reducing phosphorylation of these polypeptides. Such non-glycosylated polypeptides may be used in a wide variety of medical or cosmetic applications.

15 Claims, 2 Drawing Sheets

US 7,932,353 B2

NON-GLYCOSYLATED RECOMBINANT COLLAGEN-LIKE POLYPEPTIDES

PRIOR RELATED APPLICATIONS

This is a U.S. National Stage application of PCT/NL2006/050030 filed Feb. 22, 2006, which claims priority to European application 05075439.9 filed Feb. 23, 2005.

FIELD OF THE INVENTION

The invention relates to recombinant collagen like polypeptides that are not glycosylated. Such non-glycosylated polypeptides may be used in a wide variety of medical or cosmetic applications.

BACKGROUND OF THE INVENTION

The use of gelatin in medical applications is well known. Gelatin is used because of its low immunogenic or antigenic properties. A disadvantage of the currently used animal gelatins is that it may be contaminated with other components from the bone or hide-matrix from which it is extracted like proteins or for example prions, causing Bovine Spongiform Encephalitis (BSE).

Various methods for producing collagen-like polypeptides such as gelatin in recombinant hosts such as bacteria, plants, insects, mammalian cells or yeasts are known.

WO 01/34646 describes production of collagen-like polypeptides in a variety of hosts and contains numerous suggestions for possible modifications of such polypeptides without teaching however how such modifications can be achieved. Glycosylation is mentioned as one of several posttranslational processes that might be altered but no such alterations or means for achieving such alterations are proposed.

EP 0 926 543 describes production of recombinant collagen-like polypeptides in Pichia pastoris with high efficiency, but is silent with respect to glycosylation.

US 2003064436 describes hydroxylation as a posttranslational modification when expressing proteins in yeasts, but does not discuss glycosylation as a posttranslational modification.

Glycosylated aminoacids play an important role in (auto) immune reactions against collagen. It is suggested that they play role in T-cell recognition or T-cell binding. In human collagen N-linked glycosylation occurs on asparagine, and O-linked glycosylation on the —OH groups of hydroxylysines, serine and threonine.

It is also known that glycosylation of recombinant collagen-like polypeptides in non-human hosts differs from that in mammalian cells. The conditions under which aminoacids are glycosylated, such as the type of adjacent aminoacids, can be different, as well as the mechanism of glycosylation and thus the type of sugars attached.

Bretthauer and Castellino (Biotechnol. Appl. Biochem. (1999) 30, 193-200) describe glycosylation in the methylotrophic yeast Pichia pastoris.

Glycosylated aminoacids can also undergo phosphorylation of the sugar groups. Patents describing recombinant production of collagen-like proteins in various hosts, for example WO 01/34646 or EP 1 398 324, are silent with respect to this posttranslational modification. Phosphorylation of glycosylated aminoacids can lead to undesired high acidity of the polypeptide.

SUMMARY OF THE INVENTION

It is an object of this invention to provide non-glycosylated recombinant collagen-like polypeptides with reduced chance of eliciting immunological reactions. It is a further object of the invention to provide non-glycosylated recombinant collagen-like polypeptides that are excreted from their host cells and can be easily harvested and purified.

It is also an object of the invention to provide a non-glycosylated collagen-like polypeptide which has similar properties to natural collagen.

It is further an object of the invention to provide collagen-like polypeptides that are not phosphorylated.

It is also an object of this invention to provide stabilizers for pharmaceutical formulations with less risk of evoking immunological reactions, in particular for lyophilized formulations.

The invention presented herein is based on the surprising insight that taking measures so that glycosylation is prevented, in particular glycosylation of threonine and optionally also serine, further reduces the immunogenicity of recombinant collagen-like polypeptides while at the same time preventing or reducing phosphorylation of these peptides.

Thus the invention relates to a non-glycosylated recombinant collagen-like polypeptide comprising at least one stretch of 5 or more consecutive repeats of Gly-Xaa-Yaa triplets and in which at least 20% of the amino acids are present in the form of consecutive Gly-Xaa-Yaa triplets, characterized in that in said collagen-like polypeptide threonine is replaced by another aminoacid or threonine is absent or a glycine is adjacent to the N-terminal side of each threonine and/or adjacent to the C-terminal side of each threonine a proline is present and said recombinant collagen-like polypeptide being expressed in a micro-organism.

Preferably threonine is absent from the collagen like polypeptide or threonine is replaced by another aminoacid for example by point mutation. More preferably threonine as well as serine are absent from the collagen like polypeptide or independently threonine as well as serine are replaced by another aminoacid for example by point mutation.

DESCRIPTION OF THE INVENTION

Figure 1:
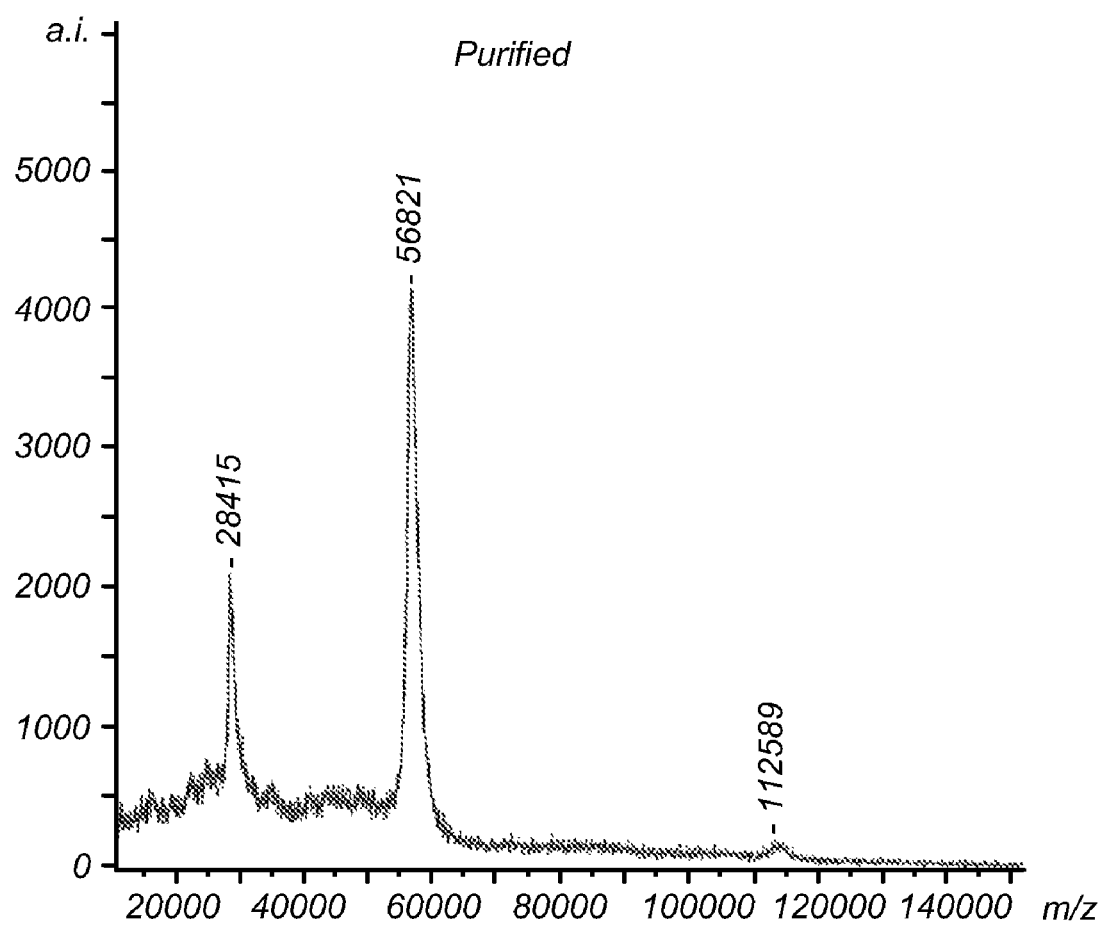
FIG. 1: MALDI-TOF mass spectrum of purified collagen-like polypeptide CLP-2

The present invention is directed at recombinantly produced collagen-like polypeptides that have reduced immunological effects and an acidity comparable to human collagens. The invention is based on the surprising insight that both these objectives are obtained by taking measures so that the collagen-like polymer remains non-glycosylated. These measures comprise one or more of replacement of threonine, and optionally serine, by another aminoacid, selection of a polypeptide sequence in which threonine, and optionally serine, is absent or placing a glycine adjacent to the N-terminal side of each threonine and/or placing a proline adjacent to the C-terminal side of each threonine and optionally a proline adjacent to the C-terminal side of at least 50% of the serines; this may be achieved by replacing the amino acids adjacent to said residues for example by point mutation.

Collagen-like recombinant or synthetic polypeptides according to the invention are preferably identical or essentially similar to natural human collagen amino acid sequences, but also non-human sequences (such as rat, rabbit, mouse etc.) can be used. Also sequences can be designed that do not occur naturally. The term "essentially similar" means that two peptide sequences, when optimally aligned, such as by the programs GAP or BESTFIT using default parameters, share at least 80 percent sequence identity, preferably at least 90 percent sequence identity, more preferably at least 95 percent sequence identity or more (e.g., 99 or 100 percent sequence identity). When calculating the percentage of sequence identity in the context of this invention the threonine residues, serine residues, the residues adjacent to the N-terminal or the C-terminal of threonine and 50% of the residues adjacent to the C-terminal side of the serine residues must be disregarded. Thus for example a natural sequence having a threonine is 100% identical to the same sequence wherein the threonine has been replaced by any other amino acid and the same is true for a sequence having an aminoacid-threonine tandem wherein said aminoacid is not a glycine compared with a natural sequence having glycine-threonine tandem (assuming the N-terminal is to the left and C-terminal to the right). GAP uses the Needleman and Wunsch global alignment algorithm to align two sequences over their entire length, maximizing the number of matches and minimizes the number of gaps. Generally, the GAP default parameters are used, with a gap creation penalty=50 (nucleotides)/8 (proteins) and gap extension penalty=3 (nucleotides)/2 (proteins).

A natural collagen molecule in its primary amino acid sequence basically consists of repeats of Gly-Xaa-Yaa triplets, thus approximately one third of the total number of amino acids is a glycine. The molecular weight of gelatin is typically large, values of the molecular weight vary from 10,000 to 300,000 daltons. The main fraction of natural gelatin molecules has a molecular weight around 90,000 daltons. The average molecular weight is higher than 90,000 daltons.

Furthermore, characteristic for collagen is the unusual high content of proline residues. Even more characteristic is that in natural collagen a number of the proline residues are hydroxylated. The most prominent site of hydroxylation is the 4-position resulting in the presence in the collagen molecule of the unusual amino acid 4-hydroxyproline. In a triplet 4-hydroxyproline is always found in the Yaa position. Very few proline residues are hydroxylated at the 3 position. In contrast with 4-hydroxyproline, 3-hydroxyproline is always found at the carboxyl side of a glycine residue, thus in the Xaa position in a triplet. Different enzymes are responsible for the formation of 3- or 4-hydroxyproline.

Based on known amino acid compositions, it is estimated that in a collagen molecule derived from a mammal, approximately 22% of the amino acids are a proline or a hydroxyproline residue. However lower contents of proline and hydroxyproline are found in fish, in particular cold water fish. A rough estimate is that proline and hydroxyproline residues are present in approximately equal amounts, thus in a collagen molecule derived from a mammal approximately 11% of the amino acids are prolines and approximately 11% are hydroxyprolines. As substantially all hydroxyproline is found in the Yaa position, it is estimated that approximately one third of all triplets in a collagen molecule comprise a hydroxyproline. The presence of the hydroxyproline residues is responsible for the fact that a collagen molecule in its secondary structure can adopt a helical conformation.

Furthermore, another amino acid present in natural collagen that is found in very few other proteins is 5-hydroxylysine. Lysine residues modified in this way are always found in the Yaa position in a triplet.

As already mentioned a predominant feature of collagens is the presence of Gly-Xaa-Yaa triplets and such triplets are also present in the collagen-like proteins of this invention. A collagen-like polypeptide comprises at least one stretch of at least 5, preferably at least 10, consecutive repeats of Gly-Xaa-Yaa triplets and at least 20% of the amino acids are present in the form of consecutive Gly-Xaa-Yaa triplets.

It is thus possible to design a protein in which Gly-Xaa-Yaa triplets or stretches of Gly-Xaa-Yaa triplets are separated by one or more amino acids without significantly altering the collagen-like character of the protein. Such collagen-like proteins are comprised by the definition of collagen-like protein of this invention.

Glycosylation can take place on the hydroxy groups of serine and threonine (O-linked glycosylation) and asparagine (N-linked glycosylation). In yeasts N-linked glycosylation of asparagine occurs on the consensus sites Asn-X-Thr or Asn-X-Ser, wherein X is any aminoacid. In human COL1A1 this sequence occurs only once as aminoacids 1365-1367 of SEQ ID NO 1 (Concepts and principles of O-linked glycosylation are described by Van den Steen et al (Critical Reviews in Biochemistry and Molecular Biology, 33(3):151-208 (1988)). Glycosylation of proteins expressed in micro-organisms is described in the literature, for example Bretthauer and Castellino (Biotechnol. Appl. Biochem. (1999) 30, 193-200) reviewed the glycosylation of *Pichia Pastoris* derived proteins.

Preferably the recombinant collagen-like polypeptide of this invention is expressed in a yeast, more preferably a methylotrophic yeast of the genus *Pichia* or *Hansenula*, most preferably *Pichia Pastoris*.

In mammalian cells glycosylation of hydroxylysines by galactose occurs. There is no information that suggests that hydroxylysines are glycosylated in micro-organisms such as yeasts. However, might there be any indication that lysine hydroxylation would occur in micro-organisms, measures can be taken to prevent the occurrence of hydroxylysines, for example by knocking out or not co-expressing lysl hydroxylase or replace lysine by pointmutation.

Glycosylation in non-mammalian cells may differ from that in mammalian cells. The nature of the aminoacids adjacent to or near serine or threonine is a factor determining the probability of glycosylation. For yeasts it is known that these conditions are different from those in mammalian cells. Besides that, the type of saccharides attached to serine or threonine differ from those in mammalian cells. Commonly in yeasts glycosylation results in the presence of N- and O-linked oligosaccharides of mannose. O-glycosylation in yeasts is different from that in mammalian cells. The oligosaccharide have a different structure which is undesired when producing collagen-like polypeptides, especially when these can contact the bloodstream.

Another posttranslational modification is phosphorylation of oligosaccharides. Phosphorylation can lead to an undesired high acidity of the collagen-like polypeptide.

In one embodiment serine as well as threonine are allowed to be present in the collagen-like polypeptide but adjacent to the C-terminal side of each threonine a glycine is present and/or adjacent to the N-terminal side of each threonine a proline is present. It is preferred that a proline is adjacent to the N-terminal side of the threonines. In this embodiment the specific sequence Asn-X-Thr and Asn-X-Ser should be avoided by, for example, avoiding the sequence when selecting natural collagen sequences or parts thereof for expression in a recombinant host, or by point mutation of the codon for Asn.

Preferably at least 50 number percent of serines are adjacent to a proline said proline being located at the N-terminal side of the serine, most preferably 100 number percent of serines have a proline adjacent to their N-terminal side.

In another embodiment the recombinant collagen-like polypeptide is free from threonine. When preparing synthetic DNA-sequences for expression of the collagen-like polypeptide no codons are used that are translated into threonine. Preferably a natural sequence or fragment is selected in which no threonine codon is present. Replacement of threonine in an aminoacid sequence derived from a natural collagen can be achieved by point-mutation. Threonine can be replaced in principle by any aminoacid. Preferably the replacement yields a GXY triplet that occurs in natural collagen. The replacing aminoacid can be serine, thus maintaining the same number of hydroxy groups in the polypeptide and maintaining high similarity to natural human collagen or the replacing aminoacid can be alanine, which lacks the hydroxyl group but has a comparable size to serine. Threonine can also be replaced by cysteine, introducing sites for crosslinking of the polypeptides.

We found unexpectedly that in a methylotrophic yeast such as *Pichia pastoris* or *Hansenula polymorpha*, in which the recombinant collagen-like polypeptide is expressed in high yields (typically more than 0.95 gram per liter, preferably more than 3 gram per liter), serines are not glycosylated.

In yet another embodiment the recombinant collagen-like polypeptide is free from threonine as well as serine to avoid any chance on glycosylation and prevent formation of phosphorylated oligosaccharides. When serine is replaced by pointmutation it is preferably replaced by alanine. Serine can also advantageously be replaced by cysteine.

In one embodiment a multimer, preferably a dimer or a trimer or a tetramer of the recombinant collagen-like polypeptide is expressed in a micro-organism as described in for example EP 1 398 324. Multimers with more than four repeats are less desired since gene-synthesis of multiple copies becomes progressively difficult with an increasing number of monomers. Preferably the recombinant collagen-like polypeptide that is the starting point of the multimer has a sequence that is essentially similar to a natural sequence. In the context of this invention such a multimer of a sequence that is essentially similar to a natural sequence, is also considered as essentially similar to natural collagen.

For example, an aminoacid sequence of 50 successive aminoacids is selected from the alpha-1 chain of human type-I collagen (COL1A1), represented by a nucleic acid sequence 'A'. Multiple repeats of the nucleic acid sequence 'A', are then inserted into a yeast expression vector and expressed as described in EP 0 926 543.

The recombinant collagen-like polypeptide of the invention can be applied in pharmaceutical or biological formulations containing physiologically active substances such as vaccines, (therapeutic) proteins, enzymes, (monoclonal) antibodies and the like. Application of such formulation generally means that the collagen-like polypeptide comprised in it is brought into the bloodstream by intravenous, intramuscular or subcutaneous infusion or injection. The low-immunogenic polypeptides of the invention are especially suitable for such applications. Preferably the inventive collagen-like polypeptides have a molecular weight of between 1.5 and 30 kilodaltons, more preferably between 3 and 25 kilodaltons. Molecular weights of more than 30 kilodalton are less preferred since these have a higher chance of eliciting an immune reaction. Too low molecular weights of less than about 3 kilodaltons have as a disadvantage that, for example, the glass transition temperature is too low which is important for lyophilized formulations.

In one embodiment the recombinant collagen-like polypeptides according to the invention have an isoelectric point of less than 8. At pH 8 lysine and arginine are positively charged, glutamic acid and aspartic acid are negatively charged and glutamine and asparagine are neutral. Glutamine and asparagine can be replaced by their corresponding acid-counterparts by point mutations in the expressed sequences or by deamidation of the recombinant structures after expression. Negatively charged groups like aspartic- or glutamic acid residues should preferably be randomly distributed over the recombinant collagen-like polypeptide. When desirable an increased number of aminoacids with negatively charged residual groups can be designed in, as long as this does not result in an increased antigenicity.

A recombinant collagen-like polypeptide can be selected or designed to have a proper isoelectric point, thus decreasing the clearance rate from blood circulation. By preparing a multimer of such a recombinant collagen-like polypeptide this effect is even improved, while maintaining the desired isoelectric point. The isoelectric point is less than 8, preferably less than 7, more preferably less than 6 even more preferably less than 5. More preferably the isoelectric point of the collagen-like polypeptide is at least more than 3, more preferably more than 4. Preferred ranges according to the invention are therefore collagen-like polypeptides having an isoelectric point of (at least) to (at most): 3-8, 4-8, 3-7, 4-7, 3-6, 4-6, 3-5 and 4-5.

In another embodiment the recombinant collagen-like polypeptides according to the invention have a calculated glass transition temperature (Tg) of at least 180 degrees Celsius. The measured glass transition temperature of the composition should also be significantly higher, preferably at least about 5 degrees, more preferably at least about 10 degrees and most preferably 20 degrees Celsius higher, than the measured glass transition temperature of a control composition, which comprises native collagen peptides. "Native collagen" as used herein refers to collagen peptides or polypeptides which were not selected or synthesized to have a high glass transition temperature. In general, native collagen peptides have a calculated Tg of about 170 degrees Celsius or less.

In our studies on collagen properties we found that, although collagen has a repetitive amino acid triplet structure Gly-Xaa-Yaa, wherein a majority of the triplets contain a proline, the glass transition temperature (or Tg) is not uniformly divided over the molecule, and sequences can be selected that have a higher Tg than the average (native) collagen.

The importance of the glass transition temperature is well known in the art of freeze drying or lyophilizing of formulations containing physiologically active substances, like vaccines. In lyophilized formulations one strives for high glass transition temperature. In "Long-Term Stabilization of Biologicals" (Biotechnology vol. 12 12 Mar. 1994) F. Franks addresses the importance of high glass transition temperatures in the preservation of biological materials by freeze drying and the desire to further improve the shelf life of such materials. In the formulations for freeze drying, gelatin serves to protect the physiologically active substance whereby the presence of water molecules bound to polar groups of the amino acid residues is thought to be of importance. Residual moisture plays an important role in the shelf life of vaccines. Increased residual moisture levels decrease the glass transition temperature of a lyophilized gelatin/disaccharide composition significantly, resulting in reduced shelf life.

The average calculated glass transition temperature of native collagen is about 170 degrees Celsius, so that a polypeptide according the invention has a Tg higher than about 180 degrees, preferably higher than about 190 degrees, more preferably higher than about 200 degrees. "About" as used herein refers to a temperature range of 1-4 degrees higher and/or lower than the specified temperature.

The calculation method of the glass transition temperature was published by Y. Matveev et. al. in Food Hydrocolloids Vol. 11 no. 2 pp. 125-133, 1997. Equations 8 and 9 were used for the actual calculations:

$$T_g^{-1} = \sum_{i=1}^{20} \phi_i T_{g,i}^{-1} \text{ wherein} \tag{8}$$

$$\phi_i = n_i \Delta V_i \Big/ \sum_{i=1}^{20} n_i \Delta V_i \tag{9}$$

wherein the summations i=1 to 20 are the summations of the values for the partial values of $T_g$ and $\Delta V$ of the separate amino acids given below (V is a measure for the vd Waals volume, as described in Matveev et al. (supra)):

| No. | Amino Acid | $T_{g,i}$ (Kelvin) | $\Delta V_i$ |
|---|---|---|---|
| 1 | gly | 599 | 47.3 |
| 2 | ala | 621 | 64.4 |
| 3 | val | 931 | 98.6 |
| 4 | leu | 400 | 115.7 |
| 5 | ile | 400 | 115.7 |
| 6 | phe | 528 | 139.9 |
| 7 | pro | 423 | 88.0 |
| 8 | trp | 544 | 196.9 |
| 9 | ser | 311 | 66.1 |
| 10 | thr | 321 | 88.9 |
| 11 | met | 362 | 120.6 |
| 12 | asn | 232 | 94.6 |
| 13 | gln | 312 | 111.7 |
| 14 | cys-SH | 418 | 82.2 |
| 15 | asp | 672 | 80.1 |
| 16 | glu | 487 | 97.2 |
| 17 | tyr | 573 | 136.9 |
| 18 | his | 488 | 118.9 |
| 19 | lys | 258 | 118.1 |
| 20 | arg | 410 | 138.4 |

The model does not appear to take the presence of hydroxyproline into account. However, the correlation with measured values which are presented in the paper of Matveev et al. give a very good correlation between calculated and measured values of gelatin.

The calculated values do not match measured values for collagen-like polypeptides with lower molecular weights of less than 30,000 Daltons. In that case the measured value can be 40 degrees Celsius or more lower than the calculated values. However, the relative differences between the average Tg calculated for a hydrolysed natural gelatin and a recombinantly produced collagen-like polypeptide of comparable molecular weight is still significant.

For selecting appropriate recombinant or synthetic collagen-like peptides that contain no threonine and/or serine a starting point is for example human COL1A1 (SEQ ID NO: 1). This sequence has a Tg of 163 degrees Celsius calculated from the entire sequence.

This COL1A1 sequence still includes the signal sequence (amino acids 1-22) and the amino terminal propeptides (amino acids 23-161 and 1219-1464). The helical collagen sequence is present from amino acid 162 to amino acid 1218. Using the above formulae the average over a number of amino acids can easily be calculated. For example a sequence from about amino acid 590 to 750 of SEQ ID NO: 1 can be selected that contains no threonine but some serines and that has an average Tg of higher than 180 degrees Celsius and a molecular weight of up to about 10,000 to 13,000 Dalton. A sequence from amino acid 554 to 763 of SEQ ID NO: 1 can be selected that contains no threonine and 4 serines 2 of which have a proline on the N-terminal side. This sequence has an average Tg of about 179 degrees Celsius, an isoelectric point of about 6.6 and a molecular weight of about 18,800 Dalton. A sequence from amino acid 554 to 637 of SEQ ID NO: 1 can be selected that contains no threonine and also no serines. This sequence has an average Tg of about 189 degrees Celsius, an iso electric point of about 6.4 and a molecular weight of about 7,500 Dalton.

Polypeptide regions with the preferred average Tg and isoelectric point such as described here above can be easily calculated also from other collagen sequences, such as Col 1A-2, Col 2A-1, Col 3A-1 and so on. Such collagen sequences are readily available in the art.

It was attempted to correlate the Tg of a polypeptide fragment to its structural details. Some correlation was found with the alanine content. Although many of the areas with higher Tg coincide with elevated alanine levels, this correlation is not valid for all regions with a Tg higher than average. Still it is likely that a region with higher Tg is found when for example a polypeptide of 54 amino acids has an alanine content of more than about 1 alanine per 10 amino acids. The presence of bulky amino acid residues can have a negative effect on the Tg of a polypeptide. A correlation was made between the presence of leucine and isoleucine and the Tg. In many areas with high Tg, but not all, the concentration of these bulky amino acid residues is low, or they are absent. Bringing valine in the correlation makes it worse, suggesting that valine has less effect on the bulkiness. Considering the sizes of the side chains of the abundantly present prolines it is imaginable that leucine and isoleucine contribute more to the bulkiness than valine. Further, it is desirable that the amount of polar amino acid residues is more than 5% and more preferably more than 7% but less than 15% so that enough water molecules can be bound to protect the lyophilized physiologically active substance.

The collagen-like polypeptides according to the invention can be produced by recombinant methods as disclosed in EP-A-0926543 and EP-A-1014176. For enablement of the production and purification of collagen-like polypeptides according to the invention specific reference is made to the examples in EP-A-0926543 and EP-A-1014176. Thus the collagen-like polypeptides can be produced by expression of nucleic acid sequence encoding such polypeptide by a suitable microorganism. The process can suitably be carried out with a fungal cell or a yeast cell. Suitably the host cell is a high expression host cell like Hansenula, Trichoderma, Aspergillus, Penicillium, Neurospora or Pichia. Fungal and yeast cells are preferred to bacteria as they are less susceptible to improper expression of repetitive sequences. Most preferably the host will not have a high level of proteases that attack the collagen structure expressed. In this respect Pichia offers an example of a very suitable expression system. As disclosed in EP-A-0926543 and EP-A-1014176 specifically Pichia pastoris is used as expression system. In one embodiment the micro-organism is also transformed to include a gene for expression of prolyl-4-hydroxylase. In another embodiment the microorganism is free of active post-translational processing mechanism such as in particular hydroxylation of proline.

The selection of a suitable host cell from known industrial enzyme producing fungal host cells specifically yeast cells on the basis of the required parameters described herein rendering the host cell suitable for expression of recombinant collagen-like polypeptides suitable in compositions according to the invention in combination with knowledge regarding the host cells and the sequence to be expressed will be possible by a person skilled in the art.

With respect to the design of collagen-like polypeptides for use in the invention, several properties of the proteins are addressed. For instance it can be made sure specific amino acids, such as bulky amino acids like leucine or isoleucine which lower the average Tg, will not occur in the protein or only occur infrequently. Otherwise, as discussed above in particular with respect to alanine or polar amino acids, it can be advantageous to introduce a definite number of a specific amino acid in the collagen-like polypeptide. Yet further the iso-electric point (IEP) can be tuned by the composition of acidic and basic amino acid residues in the collagen-like polypeptides.

In order to obtain pharmaceutical compositions one or more collagen-like polypeptides of the invention are mixed with a physiologically active compound. As an aid in vitrification a saccharide can be added. Preferably this is a disaccharide like sucrose. Depending on the application also a variety of other compounds can be added like amino acids, other proteins than gelatin, etc. Thus the invention also concerns a pharmaceutical composition comprising a physiologically active agent and a non-glycosylated recombinant collagen-like polypeptide as described herein and optionally a pharmaceutically acceptable carrier.

The pharmaceutical or biological composition comprises an amount of collagen-like polypeptides which usually lies in the range from 2-60 weight %. Vaccines are examples of pharmaceutical compounds stored as freeze-dried compositions.

Vaccines are used amongst others in developing countries where the sometimes severe storage conditions for vaccines can be difficult to maintain. Stability of lyophilized vaccines is a major concern, and the World Health Organisation issues strict rules for storage of such compositions.

Physiologically active substances are for example vaccines, (therapeutic) proteins, enzymes, (monoclonal) antibodies and the like. Gelatin is a preferred stabiliser because of its known low immunogenicity. Care should be taken that the gelatin solution is made sterile, pyrogen and antigen free.

Recombinant non-glycosylated polypeptides can be applied in cosmetics, for example to protect the human skin or hair. Various cosmetic preparations for skin protection are available in the market as lotions, emulsions, creams, milks, gels and the like. These may contain oil and/or alcohol. Also aerosols or sticks are known to be used. All such cosmetic preparations may comprise the non-glycosylated polypeptide. Applying the inventive non-glycosylated polypeptide makes the use of oils or alcohols obsolete, and even helps to prevent unwanted effects like immune reactions to such substances or reduced barrier functions of the skin.

The inventive non-glycosylated polypeptide is therefore preferably applied in, but not limited to, oil-less preparations like hydrogels.

In one embodiment UV-absorbing compounds are linked to the non-glycosylated polypeptide as described in for example EP-A1-1 273 308 and WO-A1-04/075871.

EXAMPLES

Example 1

Recombinant Collagen-Like Polypeptide Containing No Threonine or Serine

An inventive collagen-like polypeptide (CLP-1) containing no threonine or serine was produced by starting with the nucleic acid sequence that encodes for a part of the gelatin amino acid sequence of human COL1A1-1 (SEQ ID NO: 1). The methods as disclosed in EP-A-0926543, EP-A-1014176 and WO01/34646 were used. The sequence of this collagen-like polypeptide CLP-1 according to the invention is given below (SEQ ID NO: 2):

```
GPPGPAGQDGRPGPPGPPGARGQAGVMGFPGPKGAAGEPGKAGERGVPGP
PGAVGPAGKDGEAGAQGPPGPAGPAGERGEQGPAG (amino acid 554 to 638 of SEQ ID NO: 1)
```

Molecular weight: 7500 Dalton, isoelectric point pI=6.4, calculated glass transition temperature Tg=190 degrees Celsius. (COL1A1-1 SEQ ID NO: 1 has a calculated Tg of 163 degrees Celsius)

In case multimers of the sequence are expressed, the last glycine (638) is preferably omitted from the sequence.

Example 2

Recombinant Collagen-Like Polypeptide Containing Both Threonine and Serine

A comparative collagen-like polypeptide containing both threonines and serines (CLP-2) was produced by starting with the nucleic acid sequence that encodes for a part of the gelatin amino acid sequence of human COL1A1-1. The methods as disclosed in EP-A-0926543, EP-A-1014176 and WO01/34646 were used. The sequence of this gelatin according to the invention is given below (SEQ ID NO: 3). CLP-2 is a trimer of a sequence selected from COL1A1, as described in EP 1398324 A Example 3

Analysis of Posttranslational Modification of a Collagen-Like Polypeptide Mass Analysis of Recombinant Proteins (MALDI-TOF-MS)

A detailed mass spectrometric analysis by MALDI-TOF (Matrix Assisted Laser Desorption Ionization mass spectrometry) was done on CLP-2 (SEQ ID NO: 3; contains both threonines and serines). Besides the intact protein also a tryptic digest, a digest with V8 protease (glu-C) and a digest with alkaline phosphatase were analysed.
Experimental Details:
Protein Digestion Lyophilised CLP-2 was dissolved in demineralised water at 20 mg/ml concentration and then subsequently diluted 10-fold in digestion buffer. Digestion buffer was 50 mM sodium phosphate at pH 7.8 for glu-C (V8) digestion and 100 mM ammonium bicarbonate pH 7.8 for trypsin digestion. 0.5 ml of the 2 mg/ml protein solution in digestion buffer was mixed with 20 µl of enzyme solution (1 mg/ml in both cases) to give a 1:50 w/w substrate:enzyme ratio. Incubation proceeded overnight at 37° C. An aliquot of the glu-C digested protein was incubated again overnight with trypsin at a ratio 1:50 w/w to give a doubly digested sample.

Alkaline Phosphatase Incubation

CLP-2 was dissolved in 50 mM carbonate buffer (pH 9.5) at a concentration of 10 mg/ml. 1 µl of alkaline phosphatase solution (Sigma, P-6774, 20 DEA units/µl) was added to 500 µl of protein solution. The mixture was incubated for two hours at 37° C. An aliquot of reacted protein was mixed 1:3 (V/V) with 50 mM bicarbonate buffer at pH 8.1 and incubated again overnight with trypsin at a ratio 1:50 w/w to give a digested sample.

As a control, casein (SIGMA) was also reacted with alkaline phosphatase in the same conditions to check if the enzyme was active.

MALDI Sample Preparation

All CLP-2 digests described above were prepared for MALDI analysis as follows: 10 µl of digest were purified/desalted by zip tips C18 (Millipore) and eluted in 3 µl of acetonitrile/0.1% TFA 1:1 (V/V). A 1 µl aliquot was mixed 1:2 with sinapinic acid matrix (saturated 3,5-Dimethoxy-4-hydroxycinnamic acid in acetonitrile/0.1% TFA 1:2 (V/V)) for linear mode analysis, while another 1 µl aliquot was mixed 1:2 with DHB matrix (20 mg/ml of 2,5 dihydroxy benzoic acid in acetonitrile/0.1% TFA 1:1 (V/V)) for reflectron mode analysis. The only exception to this preparation was the CLP-2 tryptic digest for reflectron mode. In this case, the digest was mixed directly 1:5 with matrix DHB and spotted onto the MALDI target.

For intact protein analysis before and after alkaline phosphatase (AP) treatment, the proteins (either CLP-2 or casein) were diluted 1:50 with sinapinic acid matrix and 1 µl of the mixture was spotted onto the MALDI target.

MALDI-TOF MS Analysis

MALDI-TOF MS spectra were acquired either in reflectron or linear mode on a Bruker Biflex III mass spectrometer. Linear mode was used for analysis of intact proteins or protein fragments heavier than 2000 Da, while reflectron mode was used for peptide maps in the m/z range 500-3000.

Reflectron mode provides isotopic resolution and improved mass accuracy (better than 0.5 Da), while linear mode achieves more sensitivity. Mass accuracy for linear mode with external mass calibration is better than +/−5 Da in the mass range of interest 2000-10000. With internal calibration it is possible to obtain +/−1 Da mass accuracy. For intact protein analyses in the Mw range of CLP-2, a mass accuracy of +/−0.5% is expected with external calibration.

External mass calibration was achieved with a mixture of peptide standards ranging from 1046 to 3147 Da for reflectron mode analysis, and either bovine insulin or bovine serum albumin for linear mode analysis (using a three point linear calibration consisting of the doubly charged molecule, singly charged molecule and singly charged dimer species). Bovine insulin was used to calibrate the 2000-10 000 m/z window, while bovine serum albumin to calibrate the 20 000-100 000 m/z window for intact protein measurements.

A typical MALDI-TOF mass spectrum of purified CLP-2 is given in FIG. 1. The mass of CLP-2 is found to be 56.8 kDa (+/−0.2 kDa). Also a peak is seen at the m/z=28.4 kDa. This corresponds to CLP-2 with two charges (z=2).

For comparison; the theoretical molecular mass of CLP-2 according to the sequence is 54.4 kD. Therefore the actual mass of CLP-2 is 2.4 kD larger than expected.

Figure 2:
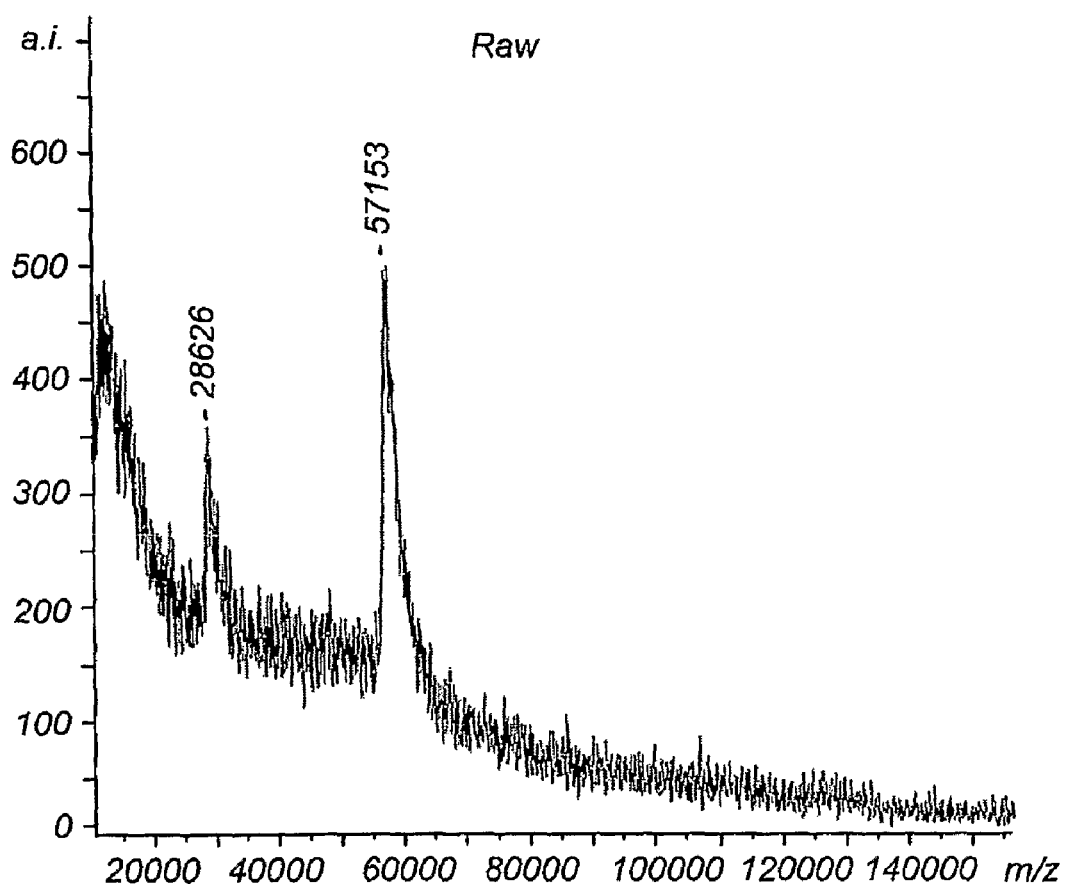
FIG. 2: MALDI-TOF mass spectrum of non-purified cell free medium collagen-like polypeptide CLP-2

The foregoing result was for purified CLP-2. There is a risk that during the down stream processing gelatin is modified. Therefore also MALDI-TOF was done of non-purified cell free medium from the 100 liter fermentation (ATO-DLO). This result is given in FIG. 2. Obviously the signal to noise ratio is less than for purified CLP-2 but it is clearly seen that a mass is obtained of 57.1 kDa. This is not significantly different from purified CLP-2 (the accuracy of MALDI-TOF is about +/−0.2 kD). Also the raw cell free medium from a 10001 fermentation was checked. This resulted in a mass of 56.7 kD (data not shown). This is also not significantly different. Therefore it can be concluded that the mass difference is not caused by the DSP process but is already present during fermentation.

Sugar Analysis (GC-MS)

A carbohydrate analysis was done to confirm the nature of glycosylation of CLP-2 by GC-MS.

To 8 milligram dry material, 100 microgram mannitol was added (internal standard). Methanolysis was performed with 1.0M HCl/MeOH for 24 hrs at 85 degrees Celsius, followed by re-N-acetylation (acetic anhydride, 24 hrs, room temperature) and trimethylsilylation (pyridine/HMDS/TMCS 5:1:1, 30 min, room temperature)

Analysis was carried out by gas-liquid chromatography on an EC-1 column (30 m×0.32 mm, Alltech), using a Chrompack CP 9002 gaschromatograph (temp. program: 140-240 degrees celsius at 4 degrees/mi) and flame-ionization detection.

Identification of the monosaccharide derivatives was confirmed by GC-MS on a Fisons Instruments GC 8060/MD 800 system (Interscience).

The sample of purified CLP-2 contained 4.7% (w/w) carbohydrate, being mainly mannose.

Phosphor Analysis (ICP-OES):

Analysis show a phosphor content of 750-1000 mg/kg in CLP-2 Only about 70 mg/kg of the total phosphor content is originating from phosphate (data not shown). The remaining part is likely from phosphorylation.

In average this means that about 1 phosphate group per molecule is present. MALDI-TOF showed that up to 11 phosphates can be present. This implies that there is a wide distribution and that a significant part of the gelatine is also non-phosphorylated.

CONCLUSIONS

Masses of CLP-2 are significantly higher than theoretical (see table 1). Tryptic digests of CLP-2 show two peaks with masses that do not match with predicted masses. These peaks show several satellite peaks with 80 mass difference. This can result from multiple phosphorylation (up to 9 phosphates). This was confirmed by ICP-OES The mass difference of these two peaks corresponds with three hexose (sugar) groups, mainly mannoses.

Alkaline phosphatase treatment shows that phosphates are not released (mass does not change). This means that bound phosphates are not mono-esterified but in the form of a phosphodiester. This has been found earlier in literature for O-glycosylation/phosphorylation of Pichia Pastoris derived proteins Recombinant gelatin production in Pichia Pastoris can give O-glycosylation in combination with phosphorylation. The glycosylation has a high mannose content and occurs on threonine. When threonine is absent in collagen-like polypeptides no glycosylation occurs. No evidence for N-glycosylation was found. O-glycosylation is different from the glycosylation pattern in human gelatins (N-type). Therefore there is a risk of immunogenic reactions when O-glycosylation is present.

TABLE 1

MALDI-TOF and sugar analysis of recombinant gelatins

| | Theoretical mass (kDa) | Measured mass (kDa) +/−0.2 | Remarks |
|---|---|---|---|
| CLP-1 | 7.5 | 7.5 | No posttranslational modification |
| CLP-2 | 54.4 | 56.8 | Post translational modification: O-glycosilation (mannose) and phosphorylation. Threonine involved. |

A carbohydrate content of 4.7% is found for CLP-2. Assuming a glycosylated fraction of 4.7% (neglecting free sugars) implies that about 16 mannose units are attached per gelatine molecule. This could be a little lower because of free sugar content. Calculating from the measured mass difference of 2400 Da (see table 1) this would give 15 mannoses per gelatine molecule (+/−1 unit). Therefore 15 mannose units per gelatine molecule is a good estimate. The distribution in number of mannose units per molecule will not be very wide because MALDI-TOF-MS gave a relatively narrow peak.

The results indicate that threonine is involved in glycosylation/phosphorylation. Serine is not likely to be involved because Ser-23 and Ser-44 in CLP-2 are not modified (confirmed by sequencing the first 44 aminoacids of CLP-2).

CLP-2 contains in total 9 threonines. Thr-9 is found to be modified. A similar position is present three times in CLP-2. If these are the only three threonines that are modified than the number of mannose units per threonine would be about 5. It is known in literature that O-glycosylation by Pichia Pastoris shows typically 2-3 mannose residues that are linked. It is therefore very well possible that other threonines in the sequence are also involved. Leaving out all the threonines is the safest way to avoid glycosylation/phosphorylation.

The invention claimed is:

1. A method of producing a collagen-like polypeptide comprising:
   (a) replacing any threonine in a naturally occurring collagen polypeptide with any other amino acid; and/or
   (b) introducing a glycine adjacent to the N-terminal side of each threonine in the naturally occurring collagen polypeptide; and/or
   (c) introducing a proline adjacent to the C-terminal side of each threonine the naturally occurring collagen; and
   (d) removing all of the Asn-X-Thr sites wherein X can be any amino acid; and
   (e) replacing any serine in a naturally occurring collagen polypeptide with any other amino acid; and
   (f) expressing the collagen-like polypeptide in a micro-organism such that the collagen-like polypeptide is not glycosylated and not phosphorylated and wherein the micro-organism is free of active post-translational hydroxylation of proline and lysine.

2. The method according to claim 1, wherein any threonine in the naturally occurring collagen is replaced by alanine or cysteine.

3. The method according to claim 1, wherein the polypeptide has an amino acid sequence that is at least 80 percent identical to an amino acid sequence of a natural collagen polypeptide.

4. The method according claim 1, wherein threonine is absent in the produced collagen-like polypeptide.

5. The method according claim 1, wherein the micro-organism is a eukaryote.

6. The method according to claim 5, wherein the eukaryote is a fungus.

7. The method according to claim 6 wherein the fungus is a yeast.

8. The method according to claim 7, wherein the yeast is a methylotrophic yeast.

9. The method according to claim 8, wherein the methylotrophic yeast is of genus *Pichia* or *Hansenula*.

10. The method according to claim 9, wherein the methylotrophic yeast comprises *Pichia pastoris, Hansenula polymorpha*, or both.

11. The method according to claim 1, wherein the collagen-like polypeptide has an isoelectric point of less than 8.

12. The method according to claim 1, wherein the polypeptide has a calculated glass-transition temperature of at least 180° C.

13. The method according to claim 1, wherein the polypeptide has a molecular weight between 1.5 kilodaltons and 30 kilodaltons.

14. The method according to claim 13, wherein the polypeptide has a molecular weight between 25 and 3 kilodaltons and 25 kilodaltons.

15. The method according to claim 14, wherein the polypeptide has a molecular weight between 10 and 3 kilodaltons and 10 kilodaltons.

* * * * *

SEQUENCE LISTING

```
<160> NUMBER OF SEQ ID NOS: 3

<210> SEQ ID NO 1
<211> LENGTH: 1464
<212> TYPE: PRT
<213> ORGANISM: human COL 1A1

<400> SEQUENCE: 1

Met Phe Ser Phe Val Asp Leu Arg Leu Leu Leu Leu Leu Ala Ala Thr
1               5                   10                  15

Ala Leu Leu Thr His Gly Gln Glu Glu Gly Gln Val Glu Gly Gln Asp
                20                  25                  30

Glu Asp Ile Pro Pro Ile Thr Cys Val Gln Asn Gly Leu Arg Tyr His
            35                  40                  45

Asp Arg Asp Val Trp Lys Pro Glu Pro Cys Arg Ile Cys Val Cys Asp
        50                  55                  60

Asn Gly Lys Val Leu Cys Asp Asp Val Ile Cys Asp Glu Thr Lys Asn
65                  70                  75                  80

Cys Pro Gly Ala Glu Val Pro Glu Gly Glu Cys Cys Pro Val Cys Pro
                85                  90                  95

Asp Gly Ser Glu Ser Pro Thr Asp Gln Glu Thr Thr Gly Val Glu Gly
                100                 105                 110

Pro Lys Gly Asp Thr Gly Pro Arg Gly Pro Arg Gly Pro Ala Gly Pro
            115                 120                 125

Pro Gly Arg Asp Gly Ile Pro Gly Gln Pro Gly Leu Pro Gly Pro Pro
        130                 135                 140

Gly Pro Pro Gly Pro Pro Gly Pro Pro Gly Leu Gly Gly Asn Phe Ala
145                 150                 155                 160

Pro Gln Leu Ser Tyr Gly Tyr Asp Glu Lys Ser Thr Gly Gly Ile Ser
                165                 170                 175

Val Pro Gly Pro Met Gly Pro Ser Gly Pro Arg Gly Leu Pro Gly Pro
                180                 185                 190

Pro Gly Ala Pro Gly Pro Gln Gly Phe Gln Gly Pro Pro Gly Glu Pro
            195                 200                 205

Gly Glu Pro Gly Ala Ser Gly Pro Met Gly Pro Arg Gly Pro Pro Gly
        210                 215                 220

Pro Pro Gly Lys Asn Gly Asp Asp Gly Glu Ala Gly Lys Pro Gly Arg
225                 230                 235                 240
```

-continued

Pro Gly Glu Arg Gly Pro Gly Pro Gln Gly Ala Arg Gly Leu Pro
            245                 250                 255

Gly Thr Ala Gly Leu Pro Gly Met Lys Gly His Arg Gly Phe Ser Gly
        260                 265                 270

Leu Asp Gly Ala Lys Gly Asp Ala Gly Pro Ala Gly Pro Lys Gly Glu
            275                 280                 285

Pro Gly Ser Pro Gly Glu Asn Gly Ala Pro Gly Gln Met Gly Pro Arg
        290                 295                 300

Gly Leu Pro Gly Glu Arg Gly Arg Pro Gly Ala Pro Gly Pro Ala Gly
305                 310                 315                 320

Ala Arg Gly Asn Asp Gly Ala Thr Gly Ala Ala Gly Pro Pro Gly Pro
                325                 330                 335

Thr Gly Pro Ala Gly Pro Pro Gly Phe Pro Gly Ala Val Gly Ala Lys
        340                 345                 350

Gly Glu Ala Gly Pro Gln Gly Pro Arg Gly Ser Glu Gly Pro Gln Gly
            355                 360                 365

Val Arg Gly Glu Pro Gly Pro Pro Gly Pro Ala Gly Ala Ala Gly Pro
        370                 375                 380

Ala Gly Asn Pro Gly Ala Asp Gly Gln Pro Gly Ala Lys Gly Ala Asn
385                 390                 395                 400

Gly Ala Pro Gly Ile Ala Gly Ala Pro Gly Phe Pro Gly Ala Arg Gly
                405                 410                 415

Pro Ser Gly Pro Gln Gly Pro Gly Gly Pro Pro Gly Pro Lys Gly Asn
            420                 425                 430

Ser Gly Glu Pro Gly Ala Pro Gly Ser Lys Gly Asp Thr Gly Ala Lys
        435                 440                 445

Gly Glu Pro Gly Pro Val Gly Val Gln Gly Pro Pro Gly Pro Ala Gly
    450                 455                 460

Glu Glu Gly Lys Arg Gly Ala Arg Gly Glu Pro Gly Pro Thr Gly Leu
465                 470                 475                 480

Pro Gly Pro Pro Gly Glu Arg Gly Gly Pro Gly Ser Arg Gly Phe Pro
                485                 490                 495

Gly Ala Asp Gly Val Ala Gly Pro Lys Gly Pro Ala Gly Glu Arg Gly
            500                 505                 510

Ser Pro Gly Pro Ala Gly Pro Lys Gly Ser Pro Gly Glu Ala Gly Arg
        515                 520                 525

Pro Gly Glu Ala Gly Leu Pro Gly Ala Lys Gly Leu Thr Gly Ser Pro
    530                 535                 540

Gly Ser Pro Gly Pro Asp Gly Lys Thr Gly Pro Pro Gly Pro Ala Gly
545                 550                 555                 560

Gln Asp Gly Arg Pro Gly Pro Pro Gly Pro Pro Gly Ala Arg Gly Gln
                565                 570                 575

Ala Gly Val Met Gly Phe Pro Gly Pro Lys Gly Ala Ala Gly Glu Pro
            580                 585                 590

Gly Lys Ala Gly Glu Arg Gly Val Pro Gly Pro Pro Gly Ala Val Gly
        595                 600                 605

Pro Ala Gly Lys Asp Gly Glu Ala Gly Ala Gln Gly Pro Pro Gly Pro
    610                 615                 620

Ala Gly Pro Ala Gly Glu Arg Gly Glu Gln Gly Pro Ala Gly Ser Pro
625                 630                 635                 640

Gly Phe Gln Gly Leu Pro Gly Pro Ala Gly Pro Pro Gly Glu Ala Gly
                645                 650                 655

Lys Pro Gly Glu Gln Gly Val Pro Gly Asp Leu Gly Ala Pro Gly Pro
            660                 665                 670

-continued

Ser Gly Ala Arg Gly Glu Arg Gly Phe Pro Gly Glu Arg Gly Val Gln
        675                 680                 685

Gly Pro Pro Gly Pro Ala Gly Pro Arg Gly Ala Asn Gly Ala Pro Gly
    690                 695                 700

Asn Asp Gly Ala Lys Gly Asp Ala Gly Ala Pro Gly Ala Pro Gly Ser
705                 710                 715                 720

Gln Gly Ala Pro Gly Leu Gln Gly Met Pro Gly Glu Arg Gly Ala Ala
                725                 730                 735

Gly Leu Pro Gly Pro Lys Gly Asp Arg Gly Asp Ala Gly Pro Lys Gly
            740                 745                 750

Ala Asp Gly Ser Pro Gly Lys Asp Gly Val Arg Gly Leu Thr Gly Pro
        755                 760                 765

Ile Gly Pro Pro Gly Pro Ala Gly Ala Pro Gly Asp Lys Gly Glu Ser
    770                 775                 780

Gly Pro Ser Gly Pro Ala Gly Pro Thr Gly Ala Arg Gly Ala Pro Gly
785                 790                 795                 800

Asp Arg Gly Glu Pro Gly Pro Pro Gly Pro Ala Gly Phe Ala Gly Pro
                805                 810                 815

Pro Gly Ala Asp Gly Gln Pro Gly Ala Lys Gly Glu Pro Gly Asp Ala
            820                 825                 830

Gly Ala Lys Gly Asp Ala Gly Pro Pro Gly Pro Ala Gly Pro Ala Gly
        835                 840                 845

Pro Pro Gly Pro Ile Gly Asn Val Gly Ala Pro Gly Ala Lys Gly Ala
    850                 855                 860

Arg Gly Ser Ala Gly Pro Pro Gly Ala Thr Gly Phe Pro Gly Ala Ala
865                 870                 875                 880

Gly Arg Val Gly Pro Pro Gly Pro Ser Gly Asn Ala Gly Pro Pro Gly
                885                 890                 895

Pro Pro Gly Pro Ala Gly Lys Glu Gly Gly Lys Gly Pro Arg Gly Glu
            900                 905                 910

Thr Gly Pro Ala Gly Arg Pro Gly Glu Val Gly Pro Pro Gly Pro Pro
        915                 920                 925

Gly Pro Ala Gly Glu Lys Gly Ser Pro Gly Ala Asp Gly Pro Ala Gly
    930                 935                 940

Ala Pro Gly Thr Pro Gly Pro Gln Gly Ile Ala Gly Gln Arg Gly Val
945                 950                 955                 960

Val Gly Leu Pro Gly Gln Arg Gly Glu Arg Gly Phe Pro Gly Leu Pro
                965                 970                 975

Gly Pro Ser Gly Glu Pro Gly Lys Gln Gly Pro Ser Gly Ala Ser Gly
            980                 985                 990

Glu Arg Gly Pro Pro Gly Pro Met Gly Pro Pro Gly Leu Ala Gly Pro
        995                 1000                1005

Pro Gly Glu Ser Gly Arg Glu Gly Ala Pro Gly Ala Glu Gly Ser
    1010                1015                1020

Pro Gly Arg Asp Gly Ser Pro Gly Ala Lys Gly Asp Arg Gly Glu
    1025                1030                1035

Thr Gly Pro Ala Gly Pro Pro Gly Ala Pro Gly Ala Pro Gly Ala
    1040                1045                1050

Pro Gly Pro Val Gly Pro Ala Gly Lys Ser Gly Asp Arg Gly Glu
    1055                1060                1065

Thr Gly Pro Ala Gly Pro Ala Gly Pro Val Gly Pro Ala Gly Ala
    1070                1075                1080

Arg Gly Pro Ala Gly Pro Gln Gly Pro Arg Gly Asp Lys Gly Glu

```
                1085                1090                1095
Thr Gly Glu Gln Gly Asp Arg Gly Ile Lys Gly His Arg Gly Phe
    1100                1105                1110
Ser Gly Leu Gln Gly Pro Pro Gly Pro Pro Gly Ser Pro Gly Glu
    1115                1120                1125
Gln Gly Pro Ser Gly Ala Ser Gly Pro Ala Gly Pro Arg Gly Pro
    1130                1135                1140
Pro Gly Ser Ala Gly Ala Pro Gly Lys Asp Gly Leu Asn Gly Leu
    1145                1150                1155
Pro Gly Pro Ile Gly Pro Pro Gly Pro Arg Gly Arg Thr Gly Asp
    1160                1165                1170
Ala Gly Pro Val Gly Pro Pro Gly Pro Pro Gly Pro Pro Gly Pro
    1175                1180                1185
Pro Gly Pro Pro Ser Ala Gly Phe Asp Phe Ser Phe Leu Pro Gln
    1190                1195                1200
Pro Pro Gln Glu Lys Ala His Asp Gly Gly Arg Tyr Tyr Arg Ala
    1205                1210                1215
Asp Asp Ala Asn Val Val Arg Asp Arg Asp Leu Glu Val Asp Thr
    1220                1225                1230
Thr Leu Lys Ser Leu Ser Gln Gln Ile Glu Asn Ile Arg Ser Pro
    1235                1240                1245
Glu Gly Ser Arg Lys Asn Pro Ala Arg Thr Cys Arg Asp Leu Lys
    1250                1255                1260
Met Cys His Ser Asp Trp Lys Ser Gly Glu Tyr Trp Ile Asp Pro
    1265                1270                1275
Asn Gln Gly Cys Asn Leu Asp Ala Ile Lys Val Phe Cys Asn Met
    1280                1285                1290
Glu Thr Gly Glu Thr Cys Val Tyr Pro Thr Gln Pro Ser Val Ala
    1295                1300                1305
Gln Lys Asn Trp Tyr Ile Ser Lys Asn Pro Lys Asp Lys Arg His
    1310                1315                1320
Val Trp Phe Gly Glu Ser Met Thr Asp Gly Phe Gln Phe Glu Tyr
    1325                1330                1335
Gly Gly Gln Gly Ser Asp Pro Ala Asp Val Ala Ile Gln Leu Thr
    1340                1345                1350
Phe Leu Arg Leu Met Ser Thr Glu Ala Ser Gln Asn Ile Thr Tyr
    1355                1360                1365
His Cys Lys Asn Ser Val Ala Tyr Met Asp Gln Thr Gly Asn
    1370                1375                1380
Leu Lys Lys Ala Leu Leu Leu Lys Gly Ser Asn Glu Ile Glu Ile
    1385                1390                1395
Arg Ala Glu Gly Asn Ser Arg Phe Thr Tyr Ser Val Thr Val Asp
    1400                1405                1410
Gly Cys Thr Ser His Thr Gly Ala Trp Gly Lys Thr Val Ile Glu
    1415                1420                1425
Tyr Lys Thr Thr Lys Thr Ser Arg Leu Pro Ile Ile Asp Val Ala
    1430                1435                1440
Pro Leu Asp Val Gly Ala Pro Asp Gln Glu Phe Gly Phe Asp Val
    1445                1450                1455
Gly Pro Val Cys Phe Leu
    1460

<210> SEQ ID NO 2
<211> LENGTH: 85
```

```
<212> TYPE: PRT
<213> ORGANISM: artificial
<220> FEATURE:
<223> OTHER INFORMATION: CLP-1 Selected collagen-like polypeptide
      containing no threonine or serine

<400> SEQUENCE: 2

Gly Pro Pro Gly Pro Ala Gly Gln Asp Gly Arg Pro Gly Pro Pro Gly
1               5                   10                  15

Pro Pro Gly Ala Arg Gly Gln Ala Gly Val Met Gly Phe Pro Gly Pro
            20                  25                  30

Lys Gly Ala Ala Gly Glu Pro Gly Lys Ala Gly Glu Arg Gly Val Pro
        35                  40                  45

Gly Pro Pro Gly Ala Val Gly Pro Ala Gly Lys Asp Gly Glu Ala Gly
    50                  55                  60

Ala Gln Gly Pro Pro Gly Pro Ala Gly Pro Ala Gly Glu Arg Gly Glu
65                  70                  75                  80

Gln Gly Pro Ala Gly
                85

<210> SEQ ID NO 3
<211> LENGTH: 617
<212> TYPE: PRT
<213> ORGANISM: artificial
<220> FEATURE:
<223> OTHER INFORMATION: CLP-2 Selected collagen-like polypeptide
      containing threonines and serines

<400> SEQUENCE: 3

Gly Pro Pro Gly Glu Pro Gly Pro Thr Gly Leu Pro Gly Pro Pro Gly
1               5                   10                  15

Glu Arg Gly Gly Pro Gly Ser Arg Gly Phe Pro Gly Ala Asp Gly Val
            20                  25                  30

Ala Gly Pro Lys Gly Pro Ala Gly Glu Arg Gly Ser Pro Gly Pro Ala
        35                  40                  45

Gly Pro Lys Gly Ser Pro Gly Glu Ala Gly Arg Pro Gly Glu Ala Gly
    50                  55                  60

Leu Pro Gly Ala Lys Gly Leu Thr Gly Ser Pro Gly Ser Pro Gly Pro
65                  70                  75                  80

Asp Gly Lys Thr Gly Pro Pro Gly Pro Ala Gly Gln Asp Gly Arg Pro
            85                  90                  95

Gly Pro Pro Gly Pro Pro Gly Ala Arg Gly Gln Ala Gly Val Met Gly
            100                 105                 110

Phe Pro Gly Pro Lys Gly Ala Ala Gly Glu Pro Gly Lys Ala Gly Glu
        115                 120                 125

Arg Gly Val Pro Gly Pro Pro Gly Ala Val Gly Pro Ala Gly Lys Asp
    130                 135                 140

Gly Glu Ala Gly Ala Gln Gly Pro Pro Gly Pro Ala Gly Pro Ala Gly
145                 150                 155                 160

Glu Arg Gly Glu Gln Gly Pro Ala Gly Ser Pro Gly Phe Gln Gly Leu
                165                 170                 175

Pro Gly Pro Ala Gly Pro Pro Gly Glu Ala Gly Lys Pro Gly Glu Gln
            180                 185                 190

Gly Val Pro Gly Asp Leu Gly Ala Pro Gly Pro Ser Gly Pro Ala Gly
        195                 200                 205

Glu Pro Gly Pro Thr Gly Leu Pro Gly Pro Pro Gly Glu Arg Gly Gly
    210                 215                 220

Pro Gly Ser Arg Gly Phe Pro Gly Ala Asp Gly Val Ala Gly Pro Lys
```

```
            225                 230                 235                 240
        Gly Pro Ala Gly Glu Arg Gly Ser Pro Gly Ala Gly Pro Lys Gly
                        245                 250                 255

Ser Pro Gly Glu Ala Gly Arg Pro Gly Glu Ala Gly Leu Pro Gly Ala
                        260                 265                 270

Lys Gly Leu Thr Gly Ser Pro Gly Ser Pro Gly Pro Asp Gly Lys Thr
                        275                 280                 285

Gly Pro Pro Gly Pro Ala Gly Gln Asp Gly Arg Pro Gly Pro Pro Gly
                        290                 295                 300

Pro Pro Gly Ala Arg Gly Gln Ala Gly Val Met Gly Phe Pro Gly Pro
        305                 310                 315                 320

Lys Gly Ala Ala Gly Glu Pro Gly Lys Ala Gly Glu Arg Gly Val Pro
                        325                 330                 335

Gly Pro Pro Gly Ala Val Gly Pro Ala Gly Lys Asp Gly Glu Ala Gly
                        340                 345                 350

Ala Gln Gly Pro Pro Gly Pro Ala Gly Pro Ala Gly Glu Arg Gly Glu
                        355                 360                 365

Gln Gly Pro Ala Gly Ser Pro Gly Phe Gln Gly Leu Pro Gly Pro Ala
                        370                 375                 380

Gly Pro Pro Gly Glu Ala Gly Lys Pro Gly Glu Gln Gly Val Pro Gly
        385                 390                 395                 400

Asp Leu Gly Ala Pro Gly Pro Ser Gly Pro Ala Gly Glu Pro Gly Pro
                        405                 410                 415

Thr Gly Leu Pro Gly Pro Pro Gly Glu Arg Gly Gly Pro Gly Ser Arg
                        420                 425                 430

Gly Phe Pro Gly Ala Asp Gly Val Ala Gly Pro Lys Gly Pro Ala Gly
                        435                 440                 445

Glu Arg Gly Ser Pro Gly Pro Ala Gly Pro Lys Gly Ser Pro Gly Glu
                        450                 455                 460

Ala Gly Arg Pro Gly Glu Ala Gly Leu Pro Gly Ala Lys Gly Leu Thr
        465                 470                 475                 480

Gly Ser Pro Gly Ser Pro Gly Pro Asp Gly Lys Thr Gly Pro Pro Gly
                        485                 490                 495

Pro Ala Gly Gln Asp Gly Arg Pro Gly Pro Pro Gly Pro Pro Gly Ala
                        500                 505                 510

Arg Gly Gln Ala Gly Val Met Gly Phe Pro Gly Pro Lys Gly Ala Ala
                        515                 520                 525

Gly Glu Pro Gly Lys Ala Gly Glu Arg Gly Val Pro Gly Pro Pro Gly
                        530                 535                 540

Ala Val Gly Pro Ala Gly Lys Asp Gly Glu Ala Gly Ala Gln Gly Pro
        545                 550                 555                 560

Pro Gly Pro Ala Gly Pro Ala Gly Glu Arg Gly Glu Gln Gly Pro Ala
                        565                 570                 575

Gly Ser Pro Gly Phe Gln Gly Leu Pro Gly Pro Ala Gly Pro Pro Gly
                        580                 585                 590

Glu Ala Gly Lys Pro Gly Glu Gln Gly Val Pro Gly Asp Leu Gly Ala
                        595                 600                 605

Pro Gly Pro Ser Gly Pro Ala Gly Gly
                        610                 615
```